United States Patent

Sakata et al.

[11] Patent Number: 5,984,683
[45] Date of Patent: Nov. 16, 1999

[54] PROSTHETIC RESTORATION AND MANUFACTURING METHOD THEREOF

[75] Inventors: Masaaki Sakata; Kenichi Shimodaira; Michio Ito, all of Nagano-ken, Japan

[73] Assignees: Injex Corporation; Matsumoto Dental College, both of Nagano-ken, Japan

[21] Appl. No.: 09/009,525

[22] Filed: Jan. 20, 1998

[30] Foreign Application Priority Data

Jan. 20, 1997 [JP] Japan ................................. 9-008067

[51] Int. Cl.$^6$ ....................................................... A61C 5/08
[52] U.S. Cl. ........................ 433/218; 433/201.1; 623/18
[58] Field of Search ............................. 433/201.1, 173, 433/218, 200.1, 208; 623/16, 18

[56] References Cited

U.S. PATENT DOCUMENTS

| | | | |
|---|---|---|---|
| 5,314,334 | 5/1994 | Panzera et al. | 433/206 |
| 5,415,704 | 5/1995 | Davidson | 623/18 |

FOREIGN PATENT DOCUMENTS

| | | |
|---|---|---|
| 0 464 951 | 1/1992 | European Pat. Off. . |
| 0 820 737 | 1/1998 | European Pat. Off. . |
| 2036946 | 12/1970 | France . |
| 4-105659 | 4/1992 | Japan . |

OTHER PUBLICATIONS

Oda, Yutaka et al. "A Study of the Method of Making Dental Prosthetic Appliances By Sintered Titanium Alloys: Effect of Copper Powder Content of Properties of Sintered Titanium Alloys," *Bulletin of Tokyo Dental College*, vol. 31, No. 1, Feb. 1990, pp. 47–52.

*Primary Examiner*—John J. Wilson
*Attorney, Agent, or Firm*—Hill & Simpson

[57] ABSTRACT

A prosthetic restoration of the invention is made from a metal material containing Ti as the main component and from 0.01 to 3 wt % of M (were M is at least one element selected from the group comprising Si, Zr, Ca, P and In). Further, in addition to these materials, from 0.01 to 4 wt % of Q (where Q is at least one element selected from the group comprising Al, Sn, V ad Cu) may be contained. On an outer surface of such a metal material, a coating layer formed of porcelain or synthetic resin or the like can be provided. Such a prosthetic restoration can be manufactured as follows. First, a model of an abutment tooth is manufactured. Next, a compound is prepared by mixing and kneading metallic powder of Ti or an alloy containing Ti, powder composed of the M or a compound containing the M and a binder. In this case, the powder composed of Q or an compound containing the Q may be added. Thereafter, thus obtained compound is built up onto the model of the abutment tooth to form a green body of the prosthetic restoration having a desired shape. Here, it is preferred that the built-up mass becomes slightly larger than the desired shape taking shrinkage of the built-up mass during sintering into consideration. Then, the built-up mass is subjected to a debinding treatment, which is then sintered to obtain a metallic sintered body. A coating layer may be formed onto the outer surface of the metallic sintered body.

29 Claims, 1 Drawing Sheet

PROSTHETIC RESTORATION AND MANUFACTURING METHOD THEREOF

BACKGROUND OF THE INVENTION

1. Field of the invention

The present invention relates to prosthetic restorations which are used on an abutment tooth, and also relates to a method for manufacturing the prosthetic restorations.

2. Description of the Prior Art

There are known prosthetic restorations which are used by being attached to an abutment tooth which has been formed by grinding down a living tooth. These prosthetic restorations are used by being bonded to and fixed on the abutment tooth with a dental cement.

Both (1) metals such as gold, silver and stainless steel and (2) ceramics such as zirconia, aluminia and sapphire have been used as structural materials for such prosthetic restorations.

However, prosthetic restorations made of ceramic materials have a disadvantage in that they have lower toughness and therefore are liable to be damaged.

Furthermore, prosthetic restorations made of noble metals such as gold and silver are very expensive. Moreover, prosthetic restorations made of stainless steel have poor biocompatibility, so that it is concerned about that they may have an adverse effect on the body such as the onset of metal allergies or the risk of carcinogenic actions due to the elusion of Ni and Cr in particular.

In view of the problems as described above, prosthetic restorations made of Ti (titanium) have been developed in recent years. Ti is light and very strong and has excellent corrosion resistance, and it does not give rise to adverse effects due to eluting materials such as those described above.

However, Ti itself does not have so good biocompatibility, and its adhesive property with respect to the abutment tooth is poor. Thus, there is a problem in that a prosthetic restoration made of Ti is liable to be disengaged due to decreasing of the fixing strength. Moreover, prosthetic restorations made of Ti also exhibit poor adhesive onto the outer surface of the prosthetic restoration, so that there is another problem in that peeling off or damage to the coating layer is liable to occur.

SUMMARY OF THE INVENTION

The object of the present invention is to provide prosthetic restorations which have excellent biocompatibility, and which are light and have sufficient hardness and mechanical strength.

Another object of the present invention is to provide prosthetic restorations which have good adhesive property with respect to the abutment tooth and which also have good adhesive property with respect to a coating layer even if such a coating layer be formed onto the prosthetic restoration.

The other object of the present invention is to provide a method of manufacturing a prosthetic restoration which can manufacture a prosthetic restoration having a complicated and fine shape easily with a good production yield and which can determine composition of a metal material from which the prosthetic restoration is formed and conditions of porosity and pore diameter in the metal material easily and precisely.

In order to achieve these objects, the present invention is directed to a prosthetic restoration made from a metal material and having a surface, wherein the composition of the metal material at least close to the surface contains Ti as the main component and also contains from 0.01 to 3 wt % of M (where M is at least one element selected from the group comprising Si, Zr, Ca, P and In).

Further, the present invention is also directed to a prosthetic restoration made from a metal material and having a surface, wherein the composition of the metal material at least close to the surface contains Ti as the main component and also contains from 0.01 to 3 wt % of M (where M is at least one element selected from the group comprising Si, Zr, Ca, P and In) and from 0.01 to 4 wt % of Q (where Q is at least one element selected from the group comprising Al, Sn, V and Cu.

In these inventions, it is preferred that the porosity of the metal material is from 0.1 to 5 vol %. In this way, the strength and hardness of the metal material can be maintained higher. Further, when a coating layer is formed, adhesive property of the prosthetic restoration with respect to the coating layer can be improved.

Further it is also preferred that the average diameter of pore (pore size) of the metal material is from 2 to 100 $\mu$m. In this way, it is possible to maintain the strength and hardness of the metal material higher, and it is also possible to prevent particles of food from entering the pores, thereby enabling to suppress the propagation of bacteria.

Furthermore, it is also preferred that the metal material is produced by means of a powder metallurgy method. According to this feature, production can be achieved easily and in good yield even with complicated and intricate shapes. Further, the conditions such as the composition and porosity of the metal material from which the prosthetic restoration is made, and the pore size, can be set easily and with a high degree of accuracy.

Moreover, it is also preferred that the prosthetic restoration further comprises a coating layer which is formed onto the surface of the metal material. In particular, it is preferred that the coating layer is formed of a ceramic material. In this way, it is possible to provide an additional value such as improvement of aesthetics by the formation of a colored coating layer. Further, since thus formed coating layer exhibits good adhesive property, peeling and damage would not be liable to occur.

Alternatively, it is also preferred that the metal material is formed by being sintered according to a powder metallurgy method, and a coating layer is formed on the surface of the metallic material, in which the thickness of the coating layer corresponds to the thickness of shrinkage upon sintering. In this way, it is possible to compensate shrinkage of the metal material during sintering process by the formation of the coating layer, thereby enabling to obtain a prosthetic restoration having a desired shape easily.

Further, the present invention is also directed to a method of manufacturing a prosthetic restoration, comprising the steps of: preparing a model of an abutment tooth; preparing a compound which is produced by mixing or compounding metal powder made of Ti or Ti alloy, metal powder of M or a compound containing M (where, M is at least one element selected from the group comprising Si, Zr, Ca, P and In) and a binding agent (binder); building up the compound onto the model of the abutment tooth so as to be a shape of a desired prosthetic restoration; and sintering the built-up compound to obtain a metallic sintered body.

Furthermore, the present invention is also directed to a method of manufacturing a prosthetic restoration, comprising the steps of: preparing a model of an abutment tooth;

preparing a compound which is produced by mixing or compounding metal powder made of Ti or Ti alloy, metal powder of M or a compound containing M (where, M is at least one element selected from the group comprising Si, Zr, Ca, P and In), metallic powder of Q or a compound containing Q (where, Q is one element selected from the group comprising Al, Sn, V and Cu) and binding agent (binder); building up the compound onto the model of the abutment tooth so as to be a desired shape of a prosthetic restoration; and sintering the built-up compound to obtain a metallic sintered body.

In these methods, it is preferred that the built-up compound is formed so as to be larger than the size of the desired prosthetic restoration taking the shrinkage of the built-up compound into account. In this way, it is possible to obtain a prosthetic restoration having a desired shape easily.

Further, it is also preferred that the method further comprises a step for forming a coating layer onto the outer surface of the metal sintered body. According to this, it is possible to provide an additional value such as improvement of aesthetics by the formation of a colored coating layer. Further, since thus formed coating layer exhibits good adhesive property, peeling and damage would not be liable to occur.

Other objects, structures and effects of the present invention will be apparent when the following description of the preferred embodiments are considered taken in conjunction with the accompanying drawings.

DETAILED DESCRIPTION OF THE PREFERRED EMBODIMENTS

Prosthetic restorations according to the present invention will be described in detail below with reference to the preferred embodiments shown in the attached drawings.

Figure 1:
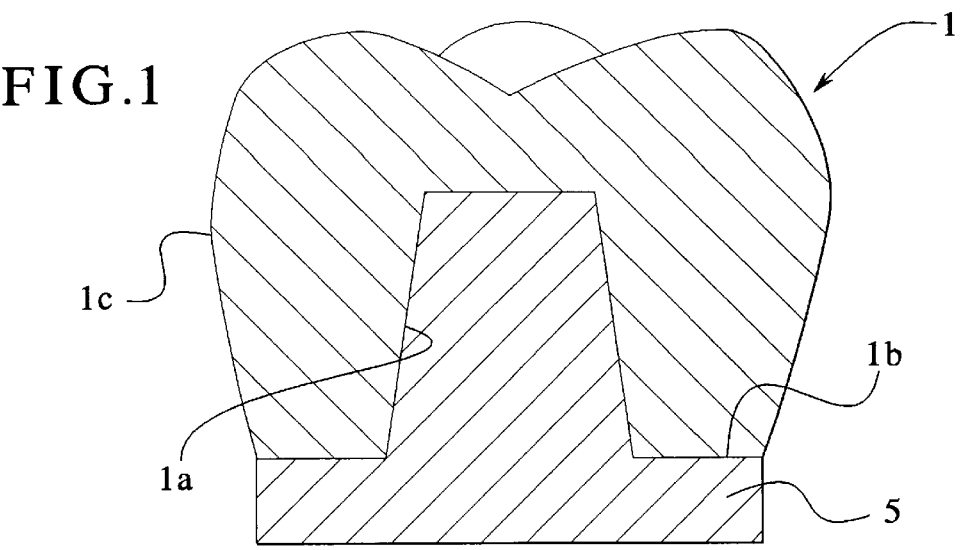
FIG. 1 is a cross sectional view which shows a first embodiment of a prosthetic restoration according to the present invention.

FIG. 1 is a cross sectional view which shows an embodiment of a prosthetic restoration according to the present invention. The prosthetic restoration (prosthesis) 1 of the present invention is used by being attached to an abutment tooth in the oral cavity. The prosthetic restoration is formed on a model of the abutment tooth 5 which has a shape corresponding to that of the abutment tooth in the oral cavity.

This prosthetic restoration 1 is made of a metal material such as described below.

the composition of the metal material from which the prosthetic restoration 1 is formed (hereinafter, referred to simply as "metal material") contains Ti as the main component and also contains a prescribed amount of M (where M is at least one element selected from the group comprising Si, Zr, Ca, P and In).

Ti is light and has high strength and hardness, and therefore Ti is not liable to deformation or damage, so that Ti has excellent durability and corrosion resistance. Further, Ti also has an advantage of inhibiting the onset of metal allergy and the like since there is very little elusion of the metal component when Ti is being used. Moreover, Ti has less luster than stainless steel, so that it is aesthetically superior to stainless steel.

In the metal material, M, that is to say at least one element selected from the group comprising Si, Zr, Ca, P and In, is present in a form where the Ti and M have formed a solid solution for example. The affinity of the prosthetic restoration 1 for the abutment tooth and the gingival tissues, that is to say its biocompatibility (bioaffinity) is improved by including the M in the metal material. Such effect is especially pronounced when Ca, P and Si are also included.

Furthermore, adhesive property of the prosthetic restoration with respect to the abutment tooth is improved by including at least one element selected from the group comprising Si, Zr, Ca, P and In in the metal material. Namely, the prosthetic restoration 1 has an inner surface 1a (which is the part to be in contact with the protruding part of the model of the abutment tooth 5) and a lower end surface 1b, and the prosthetic restoration 1 is attached to the abutment tooth 5 through these surfaces using an adhesive (dental cement for example). In this connection, if the metal material contains the M therein, the bonding strength is improved, thereby preventing the prosthetic restoration from being fallen off from the abutment tooth 5.

Moreover, in the case where a coating layer 4 as described hereinbelow is formed on the outer surface 1c of the prosthetic restoration 1, the adhesive property of the coating layer 4 with respect to the prosthetic restoration is improved by including at lest one element selected from the group comprising Si, Zr, Ca, P and In, thereby preventing peeling of or damage to the coating layer 4 from being caused.

In this connection, it is preferred for improving the aforementioned effects that Si, Zr, Ca and In are added M in the form of oxide thereof.

The amount of M included in the metal material is about 0.01 to 3 wt %, preferably about 0.03 to 2.5 wt %, and more preferably about 0.05 to 1.5 wt %.

If the amount of M included in the metal material is less than 0.01 wt %, then the effects described above are not realized satisfactorily. On the other hand, if the amount exceeds 3 wt %, then the strength and hardness of the metal material are reduced.

Moreover, in a viewpoint of improvement of the biocompatibility, it is preferable that Ca is included in the metal material, it is more preferable that both Ca and P (or Si) are included in the metal material, and it is most preferable that all of Ca, P and Si are included in the metal material.

In this connection, it is to be noted that an inclusion of Ca exhibits an effect that remarkably improves the biocompatibility of the metal material even if just a trace amount of Ca is included.

When P or Si is included along with Ca, the biocompatibility of the metal material is further improved. Further, when P and Si are included along with Ca the biocompatibility of the metal material is further improved. Furthermore, when Ca and Si are included, then the metallic luster of the metal material is further reduced, so that this contributes to improve an aesthetic effect.

The amount of Ca included in the metal material is about 0.01 to 1 wt %, preferably about 0.02 to 0.5 wt %, and more preferably about 0.3 to 0.1 wt %.

Furthermore, it is also preferred that a prescribed amount of Q (where Q is at least one element selected from the group comprising Al, Sn, V and Cu) is included in the metal material. By including the Q in the metal material, the adhesive property of the prosthetic restoration 1 with respect to the abutment tooth 5 and the adhesive property of a coating layer 4 which is formed on the outer surface 1c of the prosthetic restoration 1 can be further improved. In this connection, it is to be noted that in the case of Al it is preferred that it is added in the form of an oxide thereof for improving the aforementioned effects.

In the present invention, there is no particular limitation on the amount of Q to be contained in the metal material, but about 0.01 to 4 wt % is preferable, and 0.05 to 3 wt % is more preferable.

If the amount of Q in the metal material is less than 0.01 wt %, the improvement of the effects described above becomes insufficient. On the other hand, if the amount of Q in the metal material exceeds 4 wt %, the toughness of the metal material becomes lowered.

Furthermore, other elements, such as Fe, Cr, Pd, Co, Mo, Au, Ag and Pt for example, may be included either unavoidably or intentionally in the metal material. The addition of these elements contributes towards increasing the strength of the metal material. In this connection, it is preferred that these elements are present in the form of an alloy with Ti, an intermetallic compound or a metal oxide.

In the present invention, it is preferred that such a metal material has an appropriate porosity. Namely, it is preferable that a porosity of the metal material is about 0.1 to 5 vol %, and it is more preferable that a porosity of the metal material is about 0.3 to 4 vol %. If the porosity of the metal material is less than 0.1 vol %, then the adhesive property of a coating layer 4 with respect to the prosthetic restoration 1 is reduced when such a coating layer 4 is formed onto the prosthetic restoration 1, in particular, in the case where such a coating layer 4 is formed of a ceramic material. On the other hand, if the porosity of the metal material exceeds 5 vol %, then the strength and hardness of the metal material are reduced. In addition, since the pores tend to become coarser, particles of food, for example, can easily enter the pores, so that the propagation of bacteria is liable to occur.

Furthermore, in the present invention, there is no particular limitation on the average size (diameter) of the pores in the metal material, but it is preferable that a diameter of the pores lies within the range of from 2 to 100 $\mu$m, and it is more preferable that a diameter of the pores lies within the range of from 5 to 50 $\mu$m. With such a pore size, the strength and hardness of the metal material are well maintained, and the entry of food into cavities and the propagation of bacteria are suppressed.

The model of the abutment tooth 5 is formed of ultra-hard plaster, for instance. The model of the abutment tooth 5 is formed with dimensions slightly larger than the abutment tooth 5 in the oral cavity by taking the expansion upon hardening when molding and the thermal expansion upon sintering into account. With regard to a structural material for the model of the abutment tooth 5, it is preferred that an oxide ceramic, such as zirconia, yttria or calcia is contained. In this way, the mold release properties of the prosthetic restoration 1 which contains Ti as the main component from the model of the abutment tooth 5 are improved.

Figure 2:
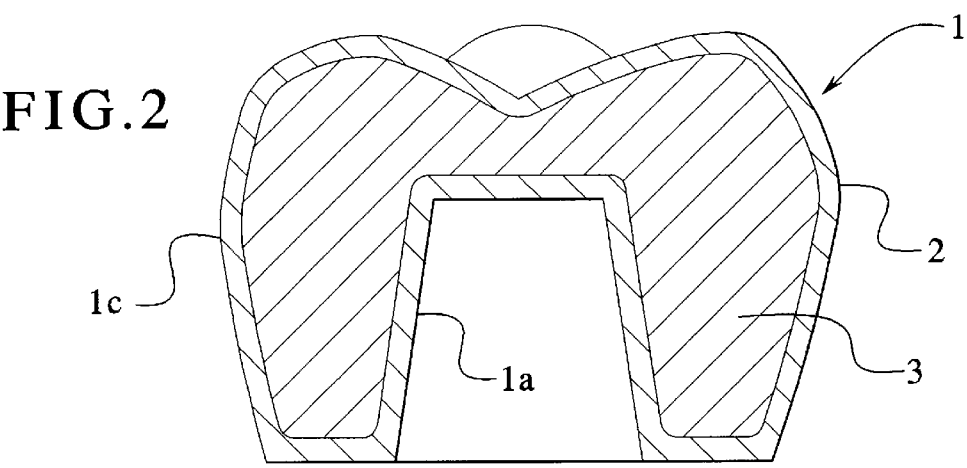
FIG. 2 is a cross sectional view which shows a second embodiment of a prosthetic restoration according to the present invention.

FIG. 2 is a cross sectional view which shows another embodiment of a prosthetic restoration of this invention. The prosthetic restoration 1 shown in this drawing has a surface layer 2, and the surface layer 2 is constructed from a metal material as described above. In this way, it is possible to exhibit the same effects as described above. Namely, it is possible to exhibit excellent biocompatibility (bioaffinity) and excellent adhesive property of the prosthetic restoration with respect to the abutment tooth 5, and excellent adhesive property of a coating layer 4 which is formed on the outer surface 1c of the prosthetic restoration 1.

Moreover, no particular limitation is imposed upon the composition or porosity of the inner part 3 of the prosthetic restoration 1 shown in FIG. 2, but in the light of improvement of the adhesive property of the surface layer 2, it is preferred that the inner part 3 is formed of Ti or an alloy which contains Ti.

Furthermore, the boundary between the inner part 3 and the surface layer 2 need not be distinct like that shown in the drawing, and the composition and porosity may vary continuously in the vicinity of this boundary.

Furthermore, with the prosthetic restoration 1 shown in FIG. 2, the surface layer 2 may be formed on either one of the inner surface (the part which is in contact with the protruding part of the model of the abutment tooth 5) 1a of the prosthetic restoration 1, or on the outer surface 1c.

Figure 3:
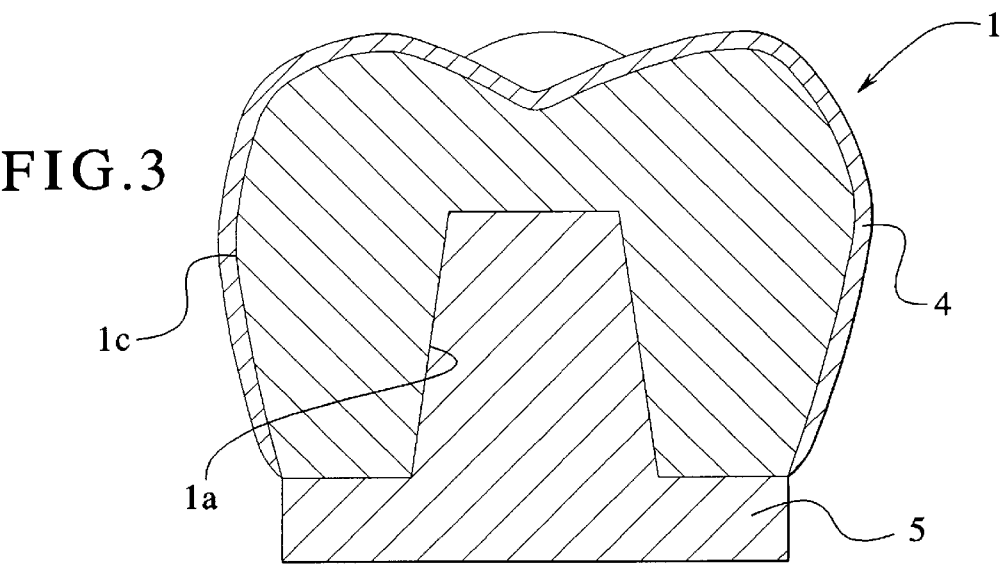
FIG. 3 is a cross sectional view which shows a third embodiment of a prosthetic restoration according to the present invention.
Figure 1:
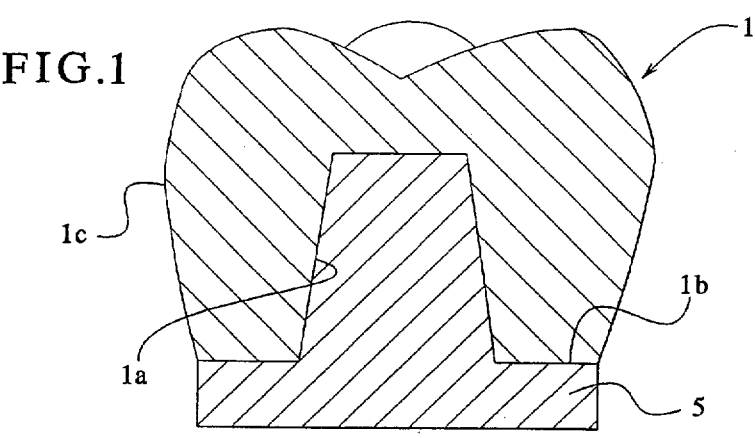
Figure 2:
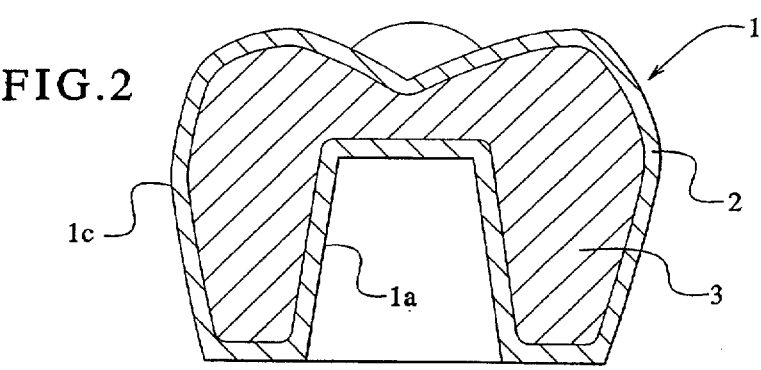
Figure 3:
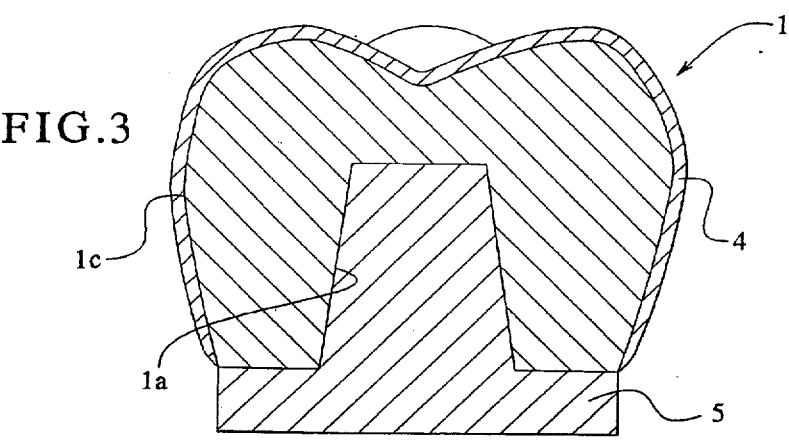

FIG. 3 is a cross sectional view which shows another embodiment of a prosthetic restoration of this invention. The prosthetic restoration 1 shown in this drawing is made with a metal material as described above, and the coating layer 4 has been formed on its outer surface 1c.

There is no limitation to the purpose of forming the coating layer 4. For example, it can be formed as a coloring layer. In this way, it is possible to manufacture a prosthetic restoration having a color close to that of natural teeth. As for a preferred example of a structural material for the coating layer 4 which has been formed for this purpose, Porcelain can be cited.

Moreover, by controlling the thickness of the coating layer 4, it is possible to compensate for the external shrinkage of the metal material during the sintering process described hereinafter (see the following process <4>) and to adjust the product to a desired shape.

No particular limitation is imposed upon the thickness of the coating layer 4, especially the thickness of a porcelain coating layer 4, but, in general, it is preferable that its thickness lies within the range of from 0.1 to 2 mm, and it is more preferable that a thickness lies within the range of from 0.1 to 1 mm.

Since the prosthetic restoration 1 of this invention is made from a metal material as described above, the adhesive property of the coating layer 4 with respect to the prosthetic restoration is good, so that peeling of and damage to the coating layer 4 is prevented.

In this regard, it is to be noted that the purpose of the formation of the coating layer 4 is not limited to the purpose as described above, and it may be formed for any purpose, for example as formation of a protective layer, a water excluding layer, a buffering layer or a lubricating layer. Further, the structural material of the coating layer 4 can be determined appropriately in accordance with the purpose for which such a coating layer is formed. For example, it may be formed from a variety of synthetic resins other than the aforementioned porcelain. Examples of such synthetic resins include curable resins such as heat curable resins, light curable resins and those which are cured by reaction, and especially rigid resins.

Further, such a coating layer 4 may be formed on the inner surface 1a.

Furthermore, such a coating layer 4 may be formed in an outer surface and/or an inner surface 1a of a prosthetic restoration which has a structure as shown in FIG. 2.

Next, a method of manufacturing a prosthetic restoration according to this invention will be described. A prosthetic restoration 1 according to the present invention is preferably manufactured using the methods of powder metallurgy in view of the ease of production, the form and dimensional stability, and the ease with which the mechanical strength, hardness and porosity of the metal material can be controlled. An example is described below.

<1> A model of the abutment tooth corresponding to the abutment tooth which has been prepared in the oral cavity is made according to the usual way.

In this connection, in order to improve releasability of the prosthetic restoration from the model of the abutment tooth 5, a coating layer (not shown in the drawing) which contains an oxide ceramic, such as zirconia, yttria or calcia for example, may be formed on the surface of the model of the abutment tooth 5.

<2> On the other hand, a metal powder comprising Ti (or Ti alloy), a powder comprising M or M compound (especially the oxide thereof), a powder comprising Q or Q compound (especially the oxide thereof), as required, and a binder (organic binder) are prepared, and then they are mixed or kneaded to produce a compound.

There is no particular limitation on the average particle size of the metal powder, but, in general, it is preferable that its average particle size lies within the range of from 1 to 100 $\mu$m, and it is more preferable that its average particle size lies within the range of from 5 to 45 $\mu$m.

Further, there is also no particular limitation on the average particle size of the powder of M or M compound and the powder of Q or Q compound, but, in general, it is preferable that their average particle size lies within the range of from 1 to 40 $\mu$m and it is more preferable that their average particle size lies within the range of from 5 to 25 $\mu$m.

The compounding ratio of M or M compound or Q or Q compound with respect to the metal powder are determined such that the amount of M and Q of the metal material in the final composition lies within the ranges as described earlier.

Examples of the binder include various thermoplastic resins, for example polyolefins such as polyethylene, polypropylene and ethylene-vinyl acetate copolymer, acrylic resins such as polymethyl (meth)acrylate and polybutyl (meth)acrylate, styrene resins such as polystyrene, polyvinyl chloride, polyamide, polyester, polyether or copolymers containing at least one of such materials, various waxes, paraffins, higher fatty acids (for example stearic acid), higher alcohols, higher fatty acid esters, higher fatty acid amides and water soluble polymeric materials such as polyvinyl alcohol and methylcellulose and the like, which may be used alone or in combination of two or more.

The amount of such binder added is preferably less than 18 wt %, and more preferably 4 to 10 wt %. If too much binder is contained, then the shrinkage that would occur upon sintering the compound which has been built up onto the model of the abutment tooth is increased, thereby the dimensional accuracy is lowered, and the porosity also tends to increase.

Furthermore, various additives, such as plasticizers, lubricants, antioxidants, debinding promoters and surfactants can be added to the compounds, as required. As for examples of plasticizers, phthalate esters (for example, DOP, DEP, DBP), adipic acid esters, trimelitic acid esters and sebacic acid esters can be cited.

<3> Next, using the compound obtained in the process <2> described above, the compound is built up manually onto the model of the abutment tooth 5 so as to be a desired shape.

In this regard, it is preferred that the built-up compound, that is to say a green body, is preferably formed so as to be slightly larger in shape and size than the intended shape and size by taking the shrinkage which would occur subsequently upon sintering into account.

However, this is not necessary in the case where a coating layer 4 is to be formed onto the prosthetic restoration later. In such a case, the shrinkage upon sintering can be compensated for (offset by) the thickness of the coating layer 4. In this case, it is not necessary to adjust the amount of the compound to be built up precisely beforehand, because it will be possible to obtain a desired shape and size easily by adjusting the thickness of a coating layer 4 when such a coating layer 4 is to be formed.

In a case where a surface layer 2 is formed, as shown in FIG. 2, the part corresponding to the inner part 3 can be formed from a compound of any composition, for example, and the part corresponding to the surface layer 2 should be formed from a compound of the aforementioned composition (which contains M and Q for example).

In this connection, it is to be noted that in this process building up of the compound and drying of the built-up compound (including solvent removal or debinding treatment) can be repeated such that a mass of the compound becomes gradually large.

<4> Then, the built-up compound that has been completed (green body) is subjected to a binder removal treatment (debinding treatment).

The debinding treatment is carried out by a heat treatment in a non-oxidizing atmosphere, that is to say in a vacuum or under reduced pressure (for example at from $1\times10^{-1}$ to $1\times10^{-6}$ Torr), or in an inert gas such as nitrogen gas or argon gas, or under a reducing atmosphere.

In this case, the heat treatment is preferably carried out under conditions at a temperature of 50 to 650° C. for a period of 0.5 to 30 hours, and more preferably at a temperature of 100 to 550° C. for a period of 1 to 15 hours.

In this regard, instead of the debinding treatment described above, simple drying, such as natural drying or hot air drying under conditions of normal temperature and humidity for example, can be carried out.

<5> Then, the built-up compound (green body) obtained in the aforementioned process <4> is sintered together with the model of the abutment tooth 5 to produce a prosthetic restoration 1 comprised of a metal sintered body. The sintering process can be carried out just once, or it may be carried out two or more times.

The sintering process is preferably carried out under the condition at a temperature of 400 to 1450° C. for a period of 1 to 24 hours, more preferably at a temperature of 500 to 1400° C. for a period of 1.5 to 10 hours, and most preferably at a temperature of 850 to 1350° C. for a period of 2 to 7 hours.

In this case, the sintering process is carried out in a non-oxidizing atmosphere, that is to say in a vacuum or under reduced pressure (for example at $1\times10^{-1}$ to $1\times10^{-6}$ Torr), or in an inert gas such as nitrogen gas or argon gas, or under a reducing atmosphere.

<6> Furthermore, a coating layer 4 is formed on the outer surface 1c of the prosthetic restoration 1, as required.

In the case where a coating layer 4 is to be formed with porcelain as described above, a slurry (compound) containing the material for the coating layer 4 is first formed as a layer by painting or dipping method, for example, and the it is dried and sintered. Alternatively, a material for the coating layer 4 may be formed as a layer on the outer surface of the built-up compound (which has not yet been sintered) of the prosthetic restoration 1 and then both may be sintered at the same time.

Further, in the case where a coating layer 4 is formed with a synthetic resin, a solution which contains the uncured resin is formed as a layer on the outer surface 1c, for example, of the prosthetic restoration 1 by painting or dipping or the like, and then the resin is hardened (cured with heat, cured with light or cured by reaction, for example).

The method which is used to form the coating layer 4 can be selected appropriately in accordance with its composition or the like, and it can be formed, for example, by means of thermal spraying, various types of plating, ion plating, sputtering, vapor deposition or CVD, in addition to the methods described above.

Furthermore, coating layers which have different compositions can be formed at different locations on the prosthetic restoration 1, or coating layers which have different compositions can be formed as laminates of two or more layers.

The formation of such coating layers 4 is preferred since it makes up for the shrinkage of the metal material in the aforementioned process <4> and enables the intended shape to be realized.

A prosthetic restoration 1 of this invention can be obtained by means of each of the processes described above.

In this regard, it is to be noted that the method for manufacturing a prosthetic restoration 1 of this invention is not limited to that described above, and the prosthetic restoration of this invention can be produced using other powder metallurgical methods. Namely, using a similar compound or slurry to the aforementioned compound, a green body is formed by a slip casting method or by Metal Injection Molding (MIM), and then thus obtained green body is subjected to a debinding treatment and a sintering process in the same way as described above, thereby obtaining a prosthetic restoration.

In a powder metallurgical method as described above, there are no problems with casting defects or melt runs that has been seen with a conventional casting method, so that prosthetic restorations can be produced easily and in good production yield.

Further, according to the method described above, it is possible to produce easily and with good dimensional accuracy even if the shape of each prosthetic restoration is complicated and intricate.

Furthermore, according to the powder metallurgical method, the M and Q contents can be adjusted with a high degree of accuracy, and the composition of the metal material from which the prosthetic restoration 1 is formed can be set as desired (and with delicacy).

Moreover, by adjusting the type of binder, the amount of the binder to be added, the conditions of the debinding treatment and the sintering conditions and the like, it is possible to desirably set the conditions for the porosity and the pore size of the metal material from which the prosthetic restoration 1 is formed.

On the basis of the facts outlined above, various conditions such as the physical properties of the metal material such as the mechanical strength and hardness, its chemical properties such as biocompatibility and corrosion resistance and its appearance can be controlled easily to the optimum conditions. In this connection, there is a case that the optimum conditions differ in respective patients or respective symptoms to which prosthetic restorations are to be attached. Therefore, since the present invention is capable of setting the optimum conditions easily so as to be suited for each of the patients, the usefulness of the present invention is especially high.

Now, it goes without saying that a prosthetic restoration 1 of this invention may be manufactured in any methods other than the powder metallurgical method described above.

Hereinbelow, actual examples of prosthetic restorations according to the present invention are described in details.

EXAMPLES 1 TO 10 AND COMPARATIVE EXAMPLES 1 AND 2

Prosthetic restorations each having the shape indicated in FIG. 1 were made as follows using a powder metallurgical method.

First of all, a model of the abutment tooth was prepared in the usual way. The composition of the model of the abutment tooth includes for example 30 wt % of $CaSO_4 \cdot 2H_2O$, 30 wt % of $ZrO_2$, 20 wt % of $Y_2O_3$ and 20 wt % of $CaO$. Moreover, the model of the abutment tooth was formed with dimensions slightly larger than the abutment tooth in the oral cavity taking the expansion upon hardening and the thermal expansion into consideration.

On the other hand, compounds for making the metal material for the prosthetic restorations were prepared with various compositions. The materials used to form the compounds are indicated below. Moreover, the compounds were mixed for 60 minutes at 90° C. using a pressing kneader.

| | |
|---|---|
| Ti Powder (Average particle size 20 µm) | 82–95 wt % |
| $SiO_2$ Powder (Average particle size 25 µm) | 0–2.0 wt % |
| $ZrO_2$ Powder (Average particle size 10 µm) | 0–0.9 wt % |
| CaO Powder (Average particle size 12 µm) | 0.01–1.4 wt % |
| $P_2O_5$ Powder (Average particle size 10 µm) | 0–1.1 wt % |
| $In_2O_3$ Powder (Average particle size 5 µm) | 0–0.8 wt % |
| $Al_2O_3$ Powder (Average particle size 30 µm) | 0–1.8 wt % |
| Sn Powder (Average particle size 20 µm) | 0–1.0 wt % |
| $V_2O_5$ Powder (Average particle size 30 µm) | 0–1.7 wt % |
| Cu Powder (Average particle size 6 µm) | 0–1.0 wt % |
| Binder etc. | |
| Polystyrene | 1.5–5.4 wt % |
| Paraffin wax | 3.0–10.8 wt % |
| Dibutyl phthalate | 0.5–1.8 wt % |

The aforementioned compounds were then built up into the form of the prescribed prosthetic restoration on the model of the abutment tooth.

Next, the completed built-up compounds (green bodies) were subjected to a debinding treatment. The debinding treatment was carried out for 3 hours at from 400 to 500° C. under a reduced pressure of $1 \times 10^{-2}$ Torr.

Next, the brown bodies which had been subjected to the debinding treatment were sintered as they are attached to the respective model of the abutment tooth. The sintering was carried out for 3 hours at 1200° C. on an argon atmosphere.

The model of the abutment tooth was then removed and prosthetic restorations which are formed of metal sintered bodies each having the shape and structure shown in FIG. 1 were obtained.

COMPARATIVE EXAMPLE 3

A prosthetic restoration having roughly the same shape as those of Examples 1 to 10 was produced suing completely annealed stainless steel (SUS 316L) which had been subjected to cutting, grinding and polishing processes.

COMPARATIVE EXAMPLE 4

A prosthetic restoration having roughly the same shape as those of Examples 1 to 10 was produced using the lost wax method, in which a stainless steel (SUS 304) raw material is melted by the high frequency melting and then it is cast under reduced pressure.

COMPARATIVE EXAMPLE 5

A prosthetic restoration having roughly the same shape as those of Examples 1 to 10 was produced using the lost wax method, in which a pure Ti raw material is melted by the high frequency melting and then it is cast under reduced pressure.

COMPARATIVE EXAMPLE 6

A prosthetic restoration having roughly the same shape as those of Examples 1 to 10 was produced by performing a discharge working on a square pillar of pure Ti using a tooth-shaped electrode.

The compositions and porosities of the metal materials of the prosthetic restorations of Examples 1 to 10 and Comparative Examples 1 to 6 are shown in the attached Table 1 and Table 2.

Moreover, the pore diameter was measured by photographing a cross section of the metal material using an electron microscope and obtaining the average pore diameter on the photograph, and then the porosity was calculated with the density ratio. As a result, it was confirmed that the average pore diameter in each metal material of Examples 1–10 and Comparative Examples 1, 2, 4 and 5 lies within the range of 2 to 100 $\mu$m, and the average pore diameter in each metal material of Comparative Examples 3 and 6 is equal to or less than 1 $\mu$m.

Next, (1) the mechanical strength, (2) the hardness, (3) the biocompatibility and (4) the adhesive property for the abutment tooth were examined using the methods outlined below, and (5) the aesthetics and (6) the ease of production of each of the prosthetic restorations in Example 1 to 10 and Comparative Examples 1 to 6 were also evaluated. The results obtained are shown in the attached Table 3 and Table 4.

(1) Mechanical Strength (Tensile Strength)

Tensile strength and elongation were measured in accordance with JIS (Japanese Industrial Standard) Z 2201 using tensile test specimens which had been produced under the same conditions as those described above.

(2) Hardness

The Vickers hardness Hv of the metal material surface was measured in accordance with JIS Z 2244.

(3) Biocompatibility

Test specimens (each having the thickness of 1 mm, and the length of 2 mm and the width of 2 mm) were produced under the same conditions as those described above. On the other hand, $2 \times 10^4$ gingival cells were inoculated onto a Petri dish having the diameter of 35 mm, each test specimen was placed on the top, 10 mM B-glycelophoshate was added and ten the specimens were incubated for 21 days. After incubation, the cells were stained with Alzarin Red and the extents to which the cells had propagated were compared using the image analyzing apparatus.

The cells which were stained red were gingival cells and more of these cells show that the specimen exhibited superior biocompatibility. An evaluation was made in accordance with the categories A where the area occupied by the cells was more than ¾ of the area of the specimen, B were it was more than ⅔ but less than ¾, C where it was more than ¼ but less than ⅔, and D were it was less than ¼.

(4) Adhesive Property for the Abutment Tooth

Each prosthetic restoration was bonded and fixed with a dental cement to an abutment tooth which was formed by cutting down an extracted tooth. Then, after 48 hours had elapsed, a stress was applied in the axial direction of the prosthetic restoration using a tensile testing machine. Thereafter, the stress upon separation from the abutment tooth (that is strength of adhesive property) was measured and an evaluation was made in the order from the largest stress in the four stages A, B, C and D.

(5) Aesthetics

The degree of luster (metallic luster) of each prosthetic restoration was assessed visually and an evaluation was made in the order in which the luster became less pronounced (inconspicuous) in the four stages A, B, C and D. The embodiment became aesthetically superior as the luster became less pronounced.

(6) Ease of Production

The effort, time, facilities and operating space required to produce each of the prosthetic restorations were evaluated overall and the results were evaluated in order from the easiest method of production in four stages A, B, C and D.

<Discussion of the Effects>

As shown in Table 3 and Table 4, it was confirmed that the prosthetic restorations of Examples 1 to 10 all had high mechanical strength and hardness, excellent biocompatibility, excellent adhesive property with the abutment tooth and excellent aesthetics, and they were very easy to produce.

On the other hand, in Comparative Example 1 it was confirmed that the M content was high and so the mechanical strength of the metal material was low. In Comparative Example 2, the Q content was high and so the toughness (elasticity) of the metal material was low.

Furthermore, in Comparative Examples 3 to 6, the biocompatibility was low and the adhesive property with the abutment tooth was also poor.

Moreover, in Comparative Examples 3 and 4 the aesthetics were poor, and in Comparative Examples 3, 5 and 6 the ease of production was also poor.

EXAMPLES 11 TO 20

Prosthetic restorations were produced in the same way as in Examples 1 to 10 as described above except that the materials indicated below were used to prepare the compounds.

Ti Powder (Average particle size 20 $\mu$m): 0–95 wt %
Ti—2 wt % Al—1 wt % V Alloy Powder (Average particle size 30 $\mu$m): 0–95 wt %
Ti—1 wt % Al—0.5 wt % Sn Alloy Powder (Average particle size 25 $\mu$m): 0–95 wt %
CaSiO$_3$ Powder (Average particle size 8 $\mu$m): 0–1.2 wt %
Ca$_3$(PO$_4$)$_2$ Powder (Average particle size 10 $\mu$m): 0–2.4 wt %
ZrO$_2$ Powder (Average particle size 10 $\mu$m): 1–0.4 wt %
In$_2$O$_3$ Powder (Average particle size 5 m): 0–0.3 wt %
Cu Powder (Average particle size 6 m): 0–1.0 wt %

| Binder etc. | |
|---|---|
| Polystyrene | 1.5–5.4 wt % |
| Paraffin wax | 3.0–10.8 wt % |
| Dibutyl phthalate | 0.5–1.8 wt % |

Next, a coating layer comprising porcelain (white) or a coating layer comprising hard synthetic resin was formed on the outer surface of each prosthetic restoration and prosthetic restorations having the shape and structure shown in FIG. 3 were obtained.

Here, the formation of the porcelain coating layer was achieved by adding 5 grams of water to 10 grams of commercially available dental porcelain ("Triple A", manufactured by Noritake Co.) to form a mixture, coating this on the surface and drying to form a paint film and then sintering. In this case, the sintering was carried out by raising the temperature from 500° C. to 760° C. at the rate of 4° C./minute under a reduced pressure of 720 Torr.

Furthermore, the formation of the synthetic resin coating layers was achieved by painting a commercially available dental resin ("Oriidex", manufactured by Sho-fusha Co,) on the surface and then curing the resin by irradiating it with visible light for 10 minutes.

The thickness of the coating layers obtained in the ways described above were about 0.3 to 1 mm. As a result, the shrinkage of the metal material upon sintering was compensated by these coating layers and thereby it was possible to adjust the prosthetic restorations to the shapes of the objects.

COMPARATIVE EXAMPLE 7

A prosthetic restoration having roughly the same form as those of Examples 11 to 20 was produced by forming a similar coating layer in the same way as described above on the outer surface of a prosthetic restoration which had been produced in the same way as in Comparative Example 3.

COMPARATIVE EXAMPLE 8

A prosthetic restoration having roughly the same form as those of Examples 11 to 20 was produced by forming a similar coating layer in the same way as described above on the outer surface of a prosthetic restoration which had been produced in the same way as in Comparative Example 4.

COMPARATIVE EXAMPLE 9

A prosthetic restoration having roughly the same form as those of Examples 11 to 20 was produced by forming a similar coating layer in the same way as described above on the outer surface of a prosthetic restoration which had been produced in the same way as in Comparative Example 5.

COMPARATIVE EXAMPLE 10

A prosthetic restoration having roughly the same form as those of Examples 11 to 20 was produced by forming a similar coating layer in the same way as described above on the outer surface of a prosthetic restoration which had been produced in the same way as in Comparative Example 6.

COMPARATIVE EXAMPLE 11

A prosthetic restoration was prepared in the same way as in Comparative Example 3 (without forming a coating layer).

The compositions and porosities of the metal materials in the prosthetic restorations of Examples 11 to 20 and Comparative Examples 7 to 11 are shown in the attached Table 5 and Table 6. In this regard, the porosity was measured in the same way as before. As a result, it was confirmed that the average pore diameter of the metal material of each of Examples 11–20 and Comparative Examples 8 and 9 lies within the range of 2 to 100 $\mu$m, and the average pore diameter of the metal material of each of Comparative Examples 7, 10 and 11 is equal to or less than 1 $\mu$m.

Next, the above-mentioned properties (1)–(6) as well as (7) an adhesive property with respect to the coating layer were measured and then evaluation was made for each of the Examples 11–20 and Comparative Examples 7–11. The results obtained are shown in the attached Table 7 and Table 8.

(7) Adhesive Property of the Coating Layer

Flex test specimens were prepared under the same conditions as those described above and each specimen was flexed through 30° and the extent of peeling of the coating layer was observed visually. An evaluation was made in order from that where there was least peeling of the coating layer in the four stages A, B, C and D.

As shown in the attached Table 7 and Table 8, it was confirmed that the prosthetic restorations of Examples 11 to 20 all had high mechanical strength and hardness, excellent biocompatibility, excellent adhesive property with the abutment tooth and excellent aesthetics, and they were very easy to produce.

On the other hand, all of Comparative Examples 7 to 10 had the same disadvantages as the aforementioned Comparative Examples 3 to 6, and the adhesive property of the coating layer was poor and there was a risk of peeling occurring in use.

Furthermore, no coating layer was formed in Comparative Example 11 and the aesthetics were especially poor.

EXAMPLES 21 to 30

Prosthetic restorations having coating layers were produced in the same way as in Examples 11 to 20 except that these prosthetic restorations have the structure shown in FIG. 2 which was produced using an internal compound (comprising pure Ti powder and binder) and a surface layer compound when building up the compound.

The average pore diameter and porosities of the surface layers were measured for each of these prosthetic restorations and the aforementioned properties (1) to (7) were measured and evaluated. As a result, it was confirmed that effects that are essentially the same as those of the corresponding Examples 11 to 20 could be obtained.

Effect of the Invention

As described above, a prosthetic restoration according to the present invention provides excellent biocompatibility and bioaffinity, is light in weight, and has adequate mechanical strength and hardness.

Furthermore, a prosthetic restoration according to the present invention has excellent adhesive property for the abutment tooth, so that separation of the prosthetic restoration is prevented. Further, if it has a coating layer, then the adhesive property with respect to the coating layer is also excellent. The effect is especially pronounced when a coating layer made of porcelain is formed.

Moreover, according to the present invention, when a prosthetic restoration is produced using the powder metallurgy method, production can be achieved easily and in good yield even with complicated and intricate shapes. Further, the conditions such as the composition and porosity of the metal material from which the prosthetic restoration is made, and the pore size, can be set easily and with a high degree of accuracy.

Finally, it should be understood that the present invention is not limited to the embodiments described above, and the scope of the present invention is determined only by the following claims.

TABLE 1

| Component | Composition of the Metal Material (remainder: Ti) [wt %] | | | | | | | | | Porosity [Vol %] |
|---|---|---|---|---|---|---|---|---|---|---|
| | Si | Zr | Ca | P | In | Al | Sn | V | Cu | |
| Example 1  | —    | —    | 0.01 | —    | —    | —    | —    | —    | —    | 0.1 |
| Example 2  | 0.15 | 0.12 | 0.03 | 0.1  | 0.1  | —    | —    | —    | —    | 0.6 |
| Example 3  | 0.4  | 0.3  | 0.1  | 0.3  | 0.4  | —    | —    | —    | —    | 1.5 |
| Example 4  | 0.6  | 0.7  | 0.5  | 0.5  | 0.7  | —    | —    | —    | —    | 4.0 |
| Example 5  | 0.01 | 0.01 | 0.01 | 0.01 | 0.01 | 0.01 | —    | —    | —    | 0.3 |
| Example 6  | 1.0  | 0.5  | 0.5  | 0.5  | 0.5  | 0.02 | 0.01 | 0.01 | 0.01 | 3.2 |
| Example 7  | 0.4  | 0.3  | 0.1  | 0.3  | 0.4  | 0.1  | 0.1  | 0.2  | 0.2  | 1.8 |
| Example 8  | 0.4  | 0.3  | 0.1  | 0.3  | 0.4  | 0.5  | 0.5  | 0.3  | 0.2  | 2.2 |
| Example 9  | 0.4  | 0.3  | 0.1  | 0.3  | 0.4  | 1.0  | 0.5  | 0.5  | 1.0  | 3.2 |
| Example 10 | 0.5  | 0.5  | 1.0  | 0.5  | 0.5  | 1.0  | 1.0  | 1.0  | 1.0  | 5.0 |

TABLE 2

| Component | Composition of the Metal Material (remainder: Ti) [wt %] | | | | | | | | | Porosity [Vol %] |
|---|---|---|---|---|---|---|---|---|---|---|
| | Si | Zr | Ca | P | In | Al | Sn | V | Cu | |
| Comp. Ex. 1 | 2.0 | 1.0 | 1.0 | —   | —   | 2.0 | 0.5 | —   | —   | 5.3 |
| Comp. Ex. 2 | 1.0 | —   | 0.5 | 0.5 | 1.5 | 2.5 | —   | 1.0 | 1.0 | 6.5 |
| Comp. Ex. 3 | Stainless Steel (SUS 316L) | | | | | | | | | 0.04 |
| Comp. Ex. 4 | Stainless Steel (SUS 304) | | | | | | | | | 5.5 |
| Comp. Ex. 5 | Pure Ti | | | | | | | | | 5.7 |
| Comp. Ex. 6 | Pure Ti | | | | | | | | | 0.05 |

TABLE 3

| | Tensile strength [MPa] | Elongation [%] | Vickers Hardness Hv | Biocompatibility | Adhesive Property for Abutment Tooth | Aesthetics | Ease of Production |
|---|---|---|---|---|---|---|---|
| Example 1  | 520 | 18 | 210 | B | B | B | A |
| Example 2  | 540 | 15 | 230 | A | A | B | A |
| Example 3  | 480 | 12 | 210 | A | A | B | A |
| Example 4  | 410 | 10 | 200 | A | A | B | A |
| Example 5  | 540 | 15 | 240 | A | A | B | A |
| Example 6  | 420 | 11 | 200 | A | A | B | A |
| Example 7  | 550 | 11 | 270 | A | A | B | A |
| Example 8  | 570 | 10 | 280 | A | A | B | A |
| Example 9  | 440 | 9  | 220 | A | A | B | A |
| Example 10 | 480 | 8  | 220 | A | A | B | A |

TABLE 4

| | Tensile strength [MPa] | Elongation [%] | Vickers Hardness Hv | Biocompatibility | Adhesive Property for Abutment Tooth | Aesthetics | Ease of Production |
|---|---|---|---|---|---|---|---|
| Comp. Ex. 1 | 370 | 5  | 180 | A | A | B | A |
| Comp. Ex. 2 | 500 | 3  | 250 | A | A | B | A |
| Comp. Ex. 3 | 480 | 35 | 100 | D | D | D | C |
| Comp. Ex. 4 | 500 | 20 | 130 | D | C | C | B |
| Comp. Ex. 5 | 520 | 2  | 260 | C | C | B | C |
| Comp. Ex. 6 | 600 | 1  | 300 | C | D | B | D |

TABLE 5

| Component | Composition of the Metal Material (remainder: Ti) [wt %] | | | | | | | | | Porosity [Vol %] | Composition of the Coating Layer |
|---|---|---|---|---|---|---|---|---|---|---|---|
| | Si | Zr | Ca | P | In | Al | Sn | V | Cu | | |
| Example 11 | 0.02 | —   | 0.03 | —   | —   | —   | —   | —   | —   | 0.3 | Porcelain |
| Example 12 | —    | 0.3 | 0.6  | 0.3 | —   | —   | —   | —   | —   | 1.0 | Porcelain |
| Example 13 | 0.1  | 0.1 | 1.1  | 0.5 | 0.2 | —   | —   | —   | —   | 1.9 | Porcelain |
| Example 14 | 0.1  | 0.2 | 0.7  | 0.3 | 0.2 | 2.0 | —   | 1.0 | —   | 3.0 | Porcelain |
| Example 15 | 0.1  | 0.2 | 0.7  | 0.3 | 0.2 | 2.0 | —   | 1.0 | 0.5 | 3.6 | Porcelain |
| Example 16 | 0.3  | 0.2 | 0.6  | 0.1 | 0.3 | 1.0 | 0.5 | —   | —   | 2.1 | Porcelain |
| Example 17 | 0.3  | 0.2 | 0.6  | 0.1 | 0.3 | 1.0 | 0.5 | —   | 1.0 | 2.4 | Porcelain |

TABLE 5-continued

| Component | Composition of the Metal Material (remainder: Ti) [wt %] | | | | | | | | | Porosity [Vol %] | Composition of the Coating Layer |
|---|---|---|---|---|---|---|---|---|---|---|---|
| | Si | Zr | Ca | P | In | Al | Sn | V | Cu | | |
| Example 18 | 0.1 | 0.1 | 1.1 | 0.5 | 0.2 | — | — | — | — | 1.9 | Synthetic Resin |
| Example 19 | 0.1 | 0.2 | 0.7 | 0.3 | 0.2 | 2.0 | — | 1.0 | 0.5 | 3.6 | Synthetic Resin |
| Example 20 | 0.3 | 0.2 | 0.6 | 0.1 | 0.3 | 1.0 | 0.5 | — | 1.0 | 2.4 | Synthetic Resin |

TABLE 6

| | Composition of the Metal Material | Porosity [Vol %] | Composition of the Coating Layer |
|---|---|---|---|
| Comp. Ex. 7 | Stainless Steel (SUS 316L) | 0.04 | Porcelain |
| Comp. Ex. 8 | Stainless Steel (SUS 304) | 5.5 | Synthetic Resin |
| Comp. Ex. 9 | Pure Ti | 5.7 | Porcelain |
| Comp. Ex. 10 | Pure Ti | 0.05 | Synthetic Resin |
| Comp. Ex. 11 | Stainless Steel (SUS 316L) | 0.04 | — |

TABLE 7

| | Tensile strength [MPa] | Elongation [%] | Vickers Hardness Hv | Biocompatibility | Adhesive Property for Abutment Tooth | Aesthetics | Ease of Production | Adhesive Property of the Coating Layer |
|---|---|---|---|---|---|---|---|---|
| Example 11 | 520 | 16 | 220 | A | A | A | A | A |
| Example 12 | 500 | 13 | 210 | A | A | A | A | A |
| Example 13 | 460 | 11 | 200 | A | A | A | A | A |
| Example 14 | 430 | 11 | 200 | A | A | A | A | A |
| Example 15 | 420 | 10 | 200 | A | A | A | A | A |
| Example 16 | 560 | 11 | 270 | A | A | A | A | A |
| Example 17 | 540 | 10 | 260 | A | A | A | A | A |
| Example 18 | 460 | 11 | 200 | A | A | A | A | B |
| Example 19 | 420 | 10 | 200 | A | A | A | A | B |
| Example 20 | 540 | 10 | 260 | A | A | A | A | B |

TABLE 8

| | Tensile strength [MPa] | Elongation [%] | Vickers Hardness Hv | Biocompatibility | Adhesive Property for Abutment Tooth | Aesthetics | Ease of Production | Adhesive Property of the Coating Layer |
|---|---|---|---|---|---|---|---|---|
| Comp. Ex. 7 | 480 | 35 | 100 | D | D | A | C | D |
| Comp. Ex. 8 | 500 | 20 | 130 | D | C | A | B | C |
| Comp. Ex. 9 | 520 | 2 | 260 | C | G | A | C | C |
| Comp. Ex. 10 | 600 | 1 | 300 | C | D | A | D | D |
| Comp. Ex. 11 | 480 | 35 | 100 | D | D | D | C | — |

What is claimed is:

1. A prosthetic restoration made from a metal material and having a surface, wherein the composition of the metal material at least close to said surface contains Ti as the main component and also contains from 0.01 to 3 wt % of M where M is at least one element selected from the group comprising Si, Zr, Ca, P and In and wherein the porosity of said metal material is from 0.1 to 5 vol %.

2. The prosthetic restoration as claim in claim 1, wherein the average diameter of pores (pore size) of the metal material is from 2 to 100 μm.

3. The prosthetic restoration as claimed in claim 1, wherein said metal material is produced by means of a powder metallurgy method.

4. The prosthetic restoration as claimed in claim 1, further comprising a coating layer which is formed onto the surface of said metal material.

5. The prosthetic restoration as claimed in claim 4, wherein the coating layer is formed of a ceramic material.

6. The prosthetic restoration as claimed in claim 1, wherein said metal material is formed by being sintered according to a powder metallurgy method, and a coating layer is formed on the surface of said metallic material, in which the thickness of said coating layer corresponds to the thickness of shrinkage upon sintering.

7. A prosthetic restoration made from a metal material and having a surface, wherein the composition of the metal material at least close to the surface contains Ti as the main component and also contains from 0.01 to 3 wt % of M where M is at least one element selected from the group comprising Si, Zr, Ca, P and In and from 0.01 to 4 wt % of Q where Q is at least one element selected from the group comprising Al, Sn, V and Cu.

8. The prosthetic restoration as claimed in claim 7, wherein the porosity of said metal material is from 0.1 to 5 vol %.

9. The prosthetic restoration as claimed in claim 8, wherein the average diameter of pores (pore size) of the metal material is from 2 to 100 μm.

10. The prosthetic restoration as claimed in claim 7, wherein said metal material is produced by means of a powder metallurgy method.

11. The prosthetic restoration as claimed claim 7, further comprising a coating layer which is formed onto the surface of said metal material.

12. The prosthetic restoration as claimed in claim 11, wherein the coating layer is formed of a ceramic material.

13. The prosthetic restoration as claimed in claim 7, wherein said metal material is formed by being sintered according to a powder metallurgy method, and a coating layer is formed on the surface of said metallic material, in which the thickness of said coating layer corresponds to the thickness of shrinkage upon sintering.

14. A method of manufacturing a prosthetic restoration, comprising the steps of:

preparing a model of an abutment tooth;

preparing a compound which is produced by mixing or compounding metal powder made of Ti or Ti alloy, metal powder of M or a compound containing M where, M is at least one element selected from the group comprising Si, Zr, Ca, P and In and a binding agent (binder);

building up the compound onto the model of the abutment tooth so as to be a shape of a desired prosthetic restoration; and sintering the built-up compound to obtain a metallic sintered body.

15. The method of manufacturing the prosthetic restoration as claimed in claim 14, wherein the built-up compound is formed so as to be larger than the size of the desired prosthetic restoration taking the shrinkage of the built-up compound into account.

16. The method of manufacturing the prosthetic restoration as claimed in claim 14, further comprising a step for forming a coating layer onto the outer surface of the metallic sintered body.

17. A method of manufacturing a prosthetic restoration, comprising the steps of:

preparing a model of an abutment tooth;

preparing a compound which is produced by mixing or compounding metal powder made of Ti or Ti alloy, metal powder of M or a compound containing M where, M is at least one element selected from the group comprising Si, Zr, Ca, P and In, metallic powder of Q or a compound containing Q where, Q is one element selected from the group comprising Al, Sn, V and Cu and binding agent (binder);

building up the compound onto the model of the abutment tooth so as to be a desired shape of a prosthetic restoration; and sintering the built-up compound to obtain a metallic sintered body.

18. The method of manufacturing the prosthetic restoration as claimed in claim 17, wherein the built-up compound is formed so as to be larger than the size of the desired prosthetic restoration taking shrinkage of the built-up compound upon sintering into account.

19. The method of manufacturing the prosthetic restoration as claimed in claim 17, further comprising a step for forming a coating layer onto the outer surface of the metallic sintered body.

20. A prosthetic restoration made from a metal material and having a surface, wherein the composition of the metal material at least close to said surface contains Ti as the main component and also contains from 0.01 to 3 wt % of M where M is at least one element selected from the group comprising Si, Zr, Ca, P and In, wherein the average diameter of pores (pore size) of the metal material is from 2 to 100 μm.

21. The prosthetic restoration as claimed in claim 20, wherein the porosity of said metal material is from 0.1 to 5 vol %.

22. The prosthetic restoration as claimed in claim 21, wherein said metal material is produced by means of a powder metallurgy method.

23. The prosthetic restoration as claimed in claim 21, further comprising a coating layer which is formed onto the surface of said metal material.

24. The prosthetic restoration as claimed in claim 23, wherein the coating layer is formed of a ceramic material.

25. The prosthetic restoration as claimed in claim 21, wherein said metal material is formed by being sintered according to a powder metallurgy method, and a coating layer is formed on the surface of said metallic material, in which the thickness of said coating layer corresponds to the thickness of shrinkage upon sintering.

26. A prosthetic restoration made from a metal material and having a surface, wherein the composition of the metal material at least close to said surface contains Ti as the main component and also contains from 0.01 to 3 wt % of M where M is at least one element selected from the group comprising Si, Zr, Ca, P and In, wherein the coating layer is formed of a ceramic material.

27. The prosthetic restoration as claimed in claim 26, wherein the porosity of said metal material is from 0.1 to 5 vol %.

28. The prosthetic restoration as claimed in clam 27, wherein the average diameter of pores (pore size) of the metal material is from 2 to 100 μm.

29. The prosthetic restoration as claimed in claim 26, wherein said metal material is produced by means of a powder metallurgy method.

* * * * *

UNITED STATES PATENT AND TRADEMARK OFFICE
CERTIFICATE OF CORRECTION

PATENT NO. : 5,984,683
DATED : November 16, 1999
INVENTOR(S) : Sakata et al.

It is certified that error appears in the above-identified patent and that said Letters Patent is hereby corrected as shown below:

The sheet of drawing consisting of figures 1-3 should be deleted to appear as per attached figures 1-3.

Signed and Sealed this

Twenty-sixth Day of December, 2000

Attest:

Q. TODD DICKINSON

*Attesting Officer*   *Director of Patents and Trademarks*